(12) United States Patent
Levin et al.

(10) Patent No.: US 12,290,380 B1
(45) Date of Patent: May 6, 2025

(54) METHOD AND SYSTEM TO MONITOR URINE OUTPUT AND MANAGE FLUID RETENTION IN A PATIENT

(71) Applicant: Reprieve Cardiovascular, Inc., Milford, MA (US)

(72) Inventors: Howard Levin, Teaneck, NY (US); Andrew Halpert, Brookline, MA (US); Mark Gelfand, New York, NY (US)

(73) Assignee: Reprieve Cardiovascular, Inc., Milford, MA (US)

( * ) Notice: Subject to any disclaimer, the term of this patent is extended or adjusted under 35 U.S.C. 154(b) by 1065 days.

(21) Appl. No.: 16/544,975

(22) Filed: Aug. 20, 2019

Related U.S. Application Data

(60) Provisional application No. 62/720,009, filed on Aug. 20, 2018.

(51) Int. Cl.
| | |
|---|---|
| *A61B 5/00* | (2006.01) |
| *A61B 5/0295* | (2006.01) |
| *A61B 5/20* | (2006.01) |
| *A61M 5/172* | (2006.01) |
| *A61M 25/00* | (2006.01) |

(52) U.S. Cl.
CPC .......... *A61B 5/4839* (2013.01); *A61B 5/0295* (2013.01); *A61B 5/208* (2013.01); *A61M 5/1723* (2013.01); *A61M 25/0017* (2013.01); *A61M 2202/0496* (2013.01)

(58) Field of Classification Search
None
See application file for complete search history.

(56) References Cited

U.S. PATENT DOCUMENTS

| | | | |
|---|---|---|---|
| 3,954,010 | A | 5/1976 | Hilblom |
| 4,132,644 | A | 1/1979 | Kolberg |
| 4,146,029 | A | 3/1979 | Ellinwood, Jr. |
| 4,204,957 | A | 5/1980 | Weickhardt |
| 4,216,462 | A | 8/1980 | McGrath et al. |
| 4,229,299 | A | 10/1980 | Savitz et al. |
| 4,261,360 | A | 4/1981 | Perez |
| 4,275,726 | A | 6/1981 | Schael |
| 4,291,692 | A | 9/1981 | Bowman et al. |

(Continued)

FOREIGN PATENT DOCUMENTS

| | | |
|---|---|---|
| EP | 1986007 | 10/2008 |
| EP | 3278833 | 2/2018 |

(Continued)

OTHER PUBLICATIONS

Eiko Furutani et al., "An Automatic Control System of the Blood Pressure of Patients Under Surgical Operation", International Journal of Control, Automation, and Systems, vol. 2, No. 1, Mar. 2004, pp. 39-54.

(Continued)

*Primary Examiner* — Matthew Kremer
(74) *Attorney, Agent, or Firm* — Perkins Coie LLP

(57) ABSTRACT

A method to treat patients suffering from fluid overload including: administrating a diuretic to the patient to increase urine output of the patient; monitoring intravascular volume of the patient; and maintaining the patient in a condition in which the intravascular volume is below a baseline intravascular volume and above a hemodynamic level by adjusting the administered diuretic.

7 Claims, 4 Drawing Sheets

(56) References Cited

U.S. PATENT DOCUMENTS

| | | | |
|---|---|---|---|
| 4,343,316 A | 8/1982 | Jespersen |
| 4,411,649 A | 10/1983 | Kamen |
| 4,448,207 A | 5/1984 | Parrish |
| 4,449,538 A | 5/1984 | Corbitt et al. |
| 4,504,263 A | 3/1985 | Steuer et al. |
| 4,658,834 A | 4/1987 | Blankenship et al. |
| 4,712,567 A | 12/1987 | Gille et al. |
| 4,728,333 A | 3/1988 | Masse et al. |
| 4,728,433 A | 3/1988 | Buck et al. |
| 4,813,925 A | 3/1989 | Anderson, Jr. et al. |
| 4,923,598 A | 5/1990 | Schal |
| 4,994,026 A | 2/1991 | Fecondini |
| 5,098,379 A | 3/1992 | Conway et al. |
| 5,176,148 A | 1/1993 | Wiest et al. |
| 5,179,862 A | 1/1993 | Lynnworth |
| 5,207,642 A | 5/1993 | Orkin et al. |
| 5,573,506 A | 11/1996 | Vasko |
| 5,586,973 A | 12/1996 | Lemaire et al. |
| 5,709,670 A | 1/1998 | Vancaillie et al. |
| 5,722,947 A | 3/1998 | Jeppsson et al. |
| 5,769,087 A | 6/1998 | Westphal et al. |
| 5,814,009 A | 9/1998 | Wheatman |
| 5,891,051 A | 4/1999 | Han et al. |
| 5,910,252 A | 6/1999 | Truitt et al. |
| 5,916,153 A | 6/1999 | Rhea, Jr. |
| 5,916,195 A | 6/1999 | Eshel et al. |
| 5,981,051 A | 11/1999 | Motegi et al. |
| 5,984,893 A | 11/1999 | Ward |
| 6,010,454 A | 1/2000 | Arieff et al. |
| 6,171,253 B1 | 1/2001 | Bullister et al. |
| 6,231,551 B1 | 5/2001 | Barbut |
| 6,272,930 B1 | 8/2001 | Crozafon |
| 6,514,226 B1 | 2/2003 | Levin et al. |
| 6,531,551 B2 | 3/2003 | Ohno et al. |
| 6,537,244 B2 | 3/2003 | Paukovits et al. |
| 6,554,791 B1 | 4/2003 | Cartledge et al. |
| 6,640,649 B1 | 11/2003 | Paz et al. |
| 6,740,072 B2 | 5/2004 | Starkweather et al. |
| 6,752,779 B2 | 6/2004 | Paukovits et al. |
| 6,796,960 B2 | 9/2004 | Cioanta et al. |
| 6,827,702 B2 | 12/2004 | Lebel et al. |
| 6,942,637 B2 | 9/2005 | Cartledge et al. |
| 7,029,456 B2 | 4/2006 | Ware et al. |
| 7,044,002 B2 | 5/2006 | Ericson et al. |
| 7,086,615 B2 | 8/2006 | Joseph |
| 7,137,964 B2 | 11/2006 | Flaherty |
| 7,278,983 B2 | 10/2007 | Ireland et al. |
| 7,727,222 B2 | 6/2010 | Da Silva |
| 7,736,354 B2 | 6/2010 | Gelfand et al. |
| 7,739,921 B1 | 6/2010 | Babcock |
| 7,758,562 B2 | 7/2010 | Gelfand |
| 7,758,563 B2 | 7/2010 | Gelfand |
| 7,837,667 B2 | 11/2010 | Gelfand |
| 7,938,817 B2 | 5/2011 | Gelfand |
| 8,007,460 B2 | 8/2011 | Gelfand |
| 8,075,513 B2 | 12/2011 | Rudko et al. |
| 8,233,957 B2 | 7/2012 | Merz et al. |
| 8,444,623 B2 | 5/2013 | Gelfand |
| 8,556,846 B2 | 10/2013 | O'Mahony et al. |
| 8,714,030 B1 | 5/2014 | Liu |
| 9,526,833 B2 | 12/2016 | Gelfand |
| 10,045,734 B2 | 8/2018 | Da Silva |
| 10,537,281 B2 | 1/2020 | Thompson et al. |
| 10,639,419 B2 * | 5/2020 | Halpert ............... A61M 5/1723 |
| 11,064,939 B2 | 7/2021 | Da Silva |
| 11,213,621 B2 | 1/2022 | Halpert |
| 11,357,446 B2 | 6/2022 | Levin et al. |
| 11,633,137 B2 | 4/2023 | Conley et al. |
| 11,696,985 B2 | 7/2023 | Halpert |
| 11,950,925 B2 | 4/2024 | Levin |
| 11,986,302 B2 | 5/2024 | Conley et al. |
| 11,992,332 B2 | 5/2024 | Da Silva |
| 2001/0029340 A1 | 10/2001 | Mault et al. |
| 2002/0025597 A1 | 2/2002 | Matsuda |
| 2002/0072647 A1 | 6/2002 | Schock et al. |
| 2002/0107536 A1 | 8/2002 | Hussein |
| 2002/0151834 A1 | 10/2002 | Utterberg |
| 2002/0161314 A1 | 10/2002 | Sarajarvi |
| 2003/0040700 A1 | 2/2003 | Hickle |
| 2003/0048185 A1 | 3/2003 | Citrenbaum et al. |
| 2003/0048432 A1 | 3/2003 | Jeng et al. |
| 2003/0114786 A1 | 6/2003 | Hiller et al. |
| 2004/0025597 A1 | 2/2004 | Ericson et al. |
| 2004/0059295 A1 | 3/2004 | Cartledge et al. |
| 2004/0081585 A1 | 4/2004 | Reid |
| 2004/0087894 A1 | 5/2004 | Flaherty |
| 2004/0122353 A1 | 6/2004 | Shahmirian et al. |
| 2004/0133187 A1 | 7/2004 | Hickle |
| 2004/0163655 A1 | 8/2004 | Gelfand et al. |
| 2004/0167415 A1 | 8/2004 | Gelfand |
| 2004/0167464 A1 | 8/2004 | Ireland et al. |
| 2004/0176703 A1 | 9/2004 | Christensen et al. |
| 2004/0193328 A1 | 9/2004 | Zaitsu et al. |
| 2004/0243075 A1 | 12/2004 | Harvie |
| 2005/0027254 A1 | 2/2005 | Vasko |
| 2005/0065464 A1 | 3/2005 | Talbot et al. |
| 2005/0085760 A1 | 4/2005 | Ware et al. |
| 2006/0052764 A1 | 3/2006 | Gelfand et al. |
| 2006/0064053 A1 | 3/2006 | Bollish et al. |
| 2006/0100743 A1 | 5/2006 | Townsend et al. |
| 2006/0184084 A1 | 8/2006 | Ware et al. |
| 2006/0235353 A1 | 10/2006 | Gelfand et al. |
| 2006/0253064 A1 * | 11/2006 | Gelfand ............... A61B 5/201 |
| | | 604/31 |
| 2006/0270971 A1 | 11/2006 | Gelfand et al. |
| 2007/0055198 A1 * | 3/2007 | O'Mahony ....... A61M 5/14212 |
| | | 604/67 |
| 2007/0088333 A1 | 4/2007 | Levin et al. |
| 2008/0027409 A1 | 1/2008 | Rudko et al. |
| 2008/0033394 A1 | 2/2008 | Gelfand et al. |
| 2008/0051764 A1 | 2/2008 | Dent et al. |
| 2008/0171966 A1 | 7/2008 | Rudko et al. |
| 2008/0221512 A1 | 9/2008 | DaSilva et al. |
| 2009/0054745 A1 | 2/2009 | Jennewine |
| 2009/0062730 A1 * | 3/2009 | Woo .................... A61M 5/1723 |
| | | 604/66 |
| 2010/0133510 A1 | 6/2010 | Kim et al. |
| 2010/0280443 A1 | 11/2010 | Gelfand et al. |
| 2010/0280444 A1 | 11/2010 | Gelfand et al. |
| 2010/0286559 A1 | 11/2010 | Paz et al. |
| 2011/0046514 A1 | 2/2011 | Greenwald et al. |
| 2011/0046516 A1 | 2/2011 | Paz et al. |
| 2011/0120231 A1 | 5/2011 | Berger |
| 2011/0196304 A1 | 8/2011 | Kramer et al. |
| 2011/0288524 A1 | 11/2011 | Gelfand et al. |
| 2012/0259308 A1 | 10/2012 | Gelfand |
| 2013/0104667 A1 | 5/2013 | Koyano |
| 2013/0235691 A1 | 9/2013 | Volker |
| 2013/0261412 A1 | 10/2013 | Reed, II |
| 2013/0274705 A1 | 10/2013 | Burnes et al. |
| 2014/0031787 A1 | 1/2014 | Burnes et al. |
| 2014/0073973 A1 * | 3/2014 | Sexton ............... A61M 5/1723 |
| | | 600/490 |
| 2014/0228755 A1 | 8/2014 | Darrah et al. |
| 2014/0260600 A1 | 9/2014 | Rike |
| 2014/0366641 A1 | 12/2014 | Jedema et al. |
| 2015/0105694 A1 | 4/2015 | Mahajan |
| 2015/0233749 A1 | 8/2015 | Wang et al. |
| 2015/0258277 A1 * | 9/2015 | Halpert ............... A61M 5/1723 |
| | | 604/503 |
| 2016/0051176 A1 | 2/2016 | Ramos et al. |
| 2016/0051750 A1 | 2/2016 | Tsoukalis |
| 2016/0136356 A1 | 5/2016 | Ribble et al. |
| 2017/0016755 A1 | 1/2017 | Boussange et al. |
| 2017/0052056 A1 | 2/2017 | Yamasaki et al. |
| 2017/0290974 A1 | 10/2017 | Tsoukalis |
| 2018/0085510 A1 | 3/2018 | Halpert et al. |
| 2018/0110455 A1 | 4/2018 | Chang et al. |
| 2018/0177945 A1 | 6/2018 | Sims et al. |
| 2018/0245967 A1 | 8/2018 | Parker et al. |
| 2019/0001057 A1 | 1/2019 | Tsoukalis |
| 2019/0038833 A1 | 2/2019 | Pirazzoli et al. |
| 2019/0262532 A1 | 8/2019 | Oh et al. |
| 2019/0321588 A1 | 10/2019 | Burnett |

(56) References Cited

U.S. PATENT DOCUMENTS

| | | |
|---|---|---|
| 2020/0230351 A1 | 7/2020 | Kelly et al. |
| 2020/0324044 A1 | 10/2020 | Gylland et al. |
| 2020/0360604 A1 | 11/2020 | Kolko et al. |
| 2020/0284234 A1 | 12/2020 | Niland |
| 2020/0405955 A1 | 12/2020 | Shah et al. |
| 2021/0077007 A1 | 3/2021 | Jouret et al. |
| 2021/0085853 A1 | 3/2021 | Chen et al. |
| 2021/0169408 A1 | 6/2021 | Levin |
| 2021/0196880 A1 | 7/2021 | O'Mahony et al. |
| 2021/0236727 A1 | 8/2021 | Levin et al. |
| 2021/0260306 A1 | 8/2021 | Gravenstein et al. |
| 2021/0283357 A1 | 9/2021 | Leonard |
| 2021/0298653 A1 | 9/2021 | Woodward et al. |
| 2022/0152302 A1 | 5/2022 | Halpert |
| 2022/0288362 A1 | 9/2022 | Porter et al. |
| 2022/0296406 A1 | 9/2022 | Keelen |
| 2022/0313158 A1 | 10/2022 | Levin et al. |
| 2022/0330866 A1 | 10/2022 | Conley et al. |
| 2022/0330867 A1 | 10/2022 | Conley et al. |
| 2022/0339622 A1 | 10/2022 | Conley et al. |
| 2023/0010793 A1 | 1/2023 | Testani |
| 2023/0414871 A1 | 12/2023 | Halpert |
| 2024/0260874 A1 | 2/2024 | Halpert |

FOREIGN PATENT DOCUMENTS

| | | |
|---|---|---|
| EP | 4108171 | 12/2022 |
| GB | 2560580 | 9/2018 |
| JP | 2008110150 | 5/2008 |
| JP | 2011-520549 | 7/2011 |
| JP | 2017-536857 | 2/2017 |
| KR | 10-2022-0035738 | 3/2022 |
| WO | WO-1996016685 | 6/1996 |
| WO | WO-1996028209 | 9/1996 |
| WO | WO-1997016220 | 5/1997 |
| WO | WO-1999006087 | 2/1999 |
| WO | 2005/102441 | 11/2005 |
| WO | WO-2006041496 | 4/2006 |
| WO | WO-2009029899 | 3/2009 |
| WO | WO-2013154783 | 10/2013 |
| WO | 2014022422 | 2/2014 |
| WO | WO-2015142617 | 9/2015 |
| WO | 2016103256 | 6/2016 |
| WO | WO-2018044959 A1 * | 3/2018 |
| WO | 2018114794 | 6/2018 |
| WO | WO-2019222485 | 11/2019 |
| WO | WO-2020033752 | 2/2020 |
| WO | WO-2022219578 | 10/2022 |

OTHER PUBLICATIONS

Delos Cosgrove III et al., "Automated Control of Postoperative Hypertension: A Prospective, Randomized Multicenter Study", 1989 by The Society of Thoracic Surgeons, 6 pages.

Samira Bell et al., "Risk of Postoperative Acute Kidney Injury in Patients Undergoing Orthopaedic Surgery—Development and Validation of Risk Score adn Effect of Acute Kidney Injury on Survival: Observational Cohort Study", BMJ: 2015:351:h56391 doi: 10.1136/bmj.h5639, 9 pages.

C.S.C. Bouman et al., "Red Blood Cell Transfusion and Furosemide in Cardiac Surgery: Friend or Foe?", The Netherlands Journal of Medicine, Dec. 2012, vol. 70, No. 10, 3 pages.

O. Goren et al., "Perioperative Acute Kidney Injury", British Journal of Anaesthesia, 115(S2): ii3-ii14 (2015), 12 pages.

Sean Josephs et al., "Perioperative Risk Assessment, Prevention, and Treatment of Acute Kidney Injury", International Anesthesiology Clinics, vol. 47, No. 4, www.anesthesiaclinics.com, pp. 89-105.

Philippe Kolh, "Renal Insufficiency After Cardiac Surgery: A Challenging Clinical Problem", European Heart Journal (2009) 30, pp. 1824-1827.

Andrea Lassnigg et al., "Lack of Renoprotective Effects of Dopamine and Furosemide During Cardiac Surgery", J Am Soc Nephrol 11: pp. 97-104, 2000.

Colin Lenihan et al., "Trends In Acute Kidney Injury, Associated Use of Dialysis, and Mortality After Cardiac Surgery, 1999 to 2008", Ann Thorac Surg. Jan. 2013; 95(1): 20-28, doi:10.1016/j.athoracsur.2012.05.131, 17 pages.

Melanie Meersch et al., "Perioperative Acute Kidney Injury: An Under-Recognized Problem", Oct. 2017, vol. 125, No. 4, www.anesthesia-analgesia.org, pp. 1223-1232.

Roderica Rui Ge Ng et al., "Identification of Modifiable Risk Factors for Acute Kidney Injury After Coronary Artery Bypass Graft Surgery in an Asian Population", The Journal of Thoracic and Cardiovascular Surgery, Apr. 2014, pp. 1356-1361.

Juan Jose Olivero et al., "Acute Kidney Injury After Cardiovascular Surgery: An Overview", MDCVJ, VIII (3) 2012, debakeyheartcenter.com/journal, pp. 31-36.

Charuhas Thakar, "Perioperative Acute Kidney Injury", Advances in Chronic Kidney Disease, vol. 20, No. 1 (January), 2013: pp. 67-75.

S. Vellinga et al., "Identfication of Modifiable Risk Factors for Acute Kidney Injury After Cardiac Surgery", The Netherlands Journal of Medicine, Dec. 2012, vol. 70, No. 10, pp. 450-454.

Mihai Gheorghiade et al., "Current Medical Therapy for Advanced Heart Failure", American Heart Journal, Jun. 1998, pp. S231-S248.

Kirkwood Adams et al., Executive Summary: HFSA 2006 Comprehensive Heart Failure Practice Guideline, Journal of Cardiac Failure, vol. 12, No. 1, 2006, pp. 10-38.

"2016 ESC Guidelines for the Diagnosis and Treatment of Acute and Chronic Heart Failure—Web Addenda", European Heart Journal, doi:10.1039/eurheartj/ehw128, 17 pages.

Teixeira et al., "Fluid Balance and Urine vol. are Independent Predictors of Mortality in Acute Kidney Injury", Critical Care 17:R14 (2013) 11 pages.

Kui Jin et al., "Intensive Monitoring of Urine Output Is Associated With Increased Detection of Acute Kidney Injury and Improved Outcomes," Chest Journal—Original Research Critical Care, 152#5, pp. 972-979 (Nov. 2017) 8 pages.

Abraham Otero, "A New Device to Automate the Monitoring of Critical Patients' Urine Output", Hindawi Publishing Corp, BioMed Research Int'l, vol. 2014, Article ID 587593, 8 pages.

Adaptec Medical Devices, "Ongoing Access to Real-Time and Accurate Monitoring of Urine Output Could Improve Management of Critically Ill Patients," Clinical Literature Review, (2016) 8 pages.

Mayo Clinic, "Creatinine Test", Mayo Foundation for Medical Education and Research (MFMER) (downloaded Aug. 16, 2018).

Stickler et al., "A Sensor to Detect the Early Stages in the Development of Crystalline Proteus mirabilis Biofilm on Indwelling Bladder Catheters", Journal of Clinical Microbiology, Apr. 2006, p. 1540-1542.

Antonio Tricoli, "Miniaturized Bio-and Chemical-Sensors for Point-of-Care Monitoring of Chronic Kidney Diseases," Sensors 2018, 18, 942; (Mar. 22, 2018) 18 pages.

Kambiz Kalantari, "Assessment of Intravascular Volume Status and Volume Responsiveness in Critically Ill Patients," Kidney International (2013) 83, 1017-1028 (Jan. 9, 2013) 12 pages.

David Farcy, "Review: Pitfalls in Using Central Venous Pressure as a Marker of Fluid Responsiveness," Emergency Medicine. Jan. 2016;48(1):18-28, 15 pages.

Barbara Lara, "Accurate Monitoring of Intravascular Fluid Volume: A Novel Application of Intrathoracic Impedance Measures for the Guidance of Volume Reduction Therapy," IJC Heart & Vasculature, 8 (2015) pp. 47-51, 5 pages.

Vivane Conradds, "Sensitivity and Positive Predictive Value of Implantable Intrathoracic Impedance Monitoring as a Predictor of Heart Failure Hospitalizations: The SENSE-HF Trial," European Heart Journal (2011) 32, 2266-2273, 8 pages.

Sheldon Magder et al., "The Clinical Role of Central Venous Pressure Measurements", Journal of Intensive Care Medicine 22(1); 207, 8 pages.

Se Won Oh et al., "Loop Diuretics in Clinical Practice", Electrolytes & Blood Pressure, www.ncbi.nlm.nih.gov/pmc/articles/PMC4520883, printed Mar. 25, 2019, 6 pages.

Alison Shepherd, "Measuring and Managing Fluid Balance", Nursing Times, vol. 107, No. 28, pp. 12-16 (Jul. 19, 2011) 5 pages.

(56) References Cited

OTHER PUBLICATIONS

Phillips et al., "Measurement of sodium ion concentration in undiluted urine with cation-selective polymeric membrane electrodes after the removal of interfering compounds", Talanta, Elsevier, Amsterdam, NL, vol. 74, No. 2, Nov. 15, 2007, pp. 255-264.
U.S. Appl. No. 18/434,540, filed Feb. 6, 2024, Halpert.
U.S. Appl. No. 18/595,182, filed Mar. 4, 2024, Levin.
U.S. Appl. No. 18/637,340, filed Apr. 16, 2024, Conley et al..
U.S. Appl. No. 18/641,241, filed Apr. 19, 2024, Da Silva.
Allen et al., "Continuous Versus Bolus Dosing of Furosemide for Patients Hospitalized for Heart Failure," American Journal of Cardiology, 105(12):1794-1794, 2010.
Baliga, "Diuretic Therapy for Heart Failure Patients," American College of Cardiology, 75:1178-1195, 2020.
Brater, "Diuretic Therapy," New England Journal of Medicine, 339:387-395, 1998.
Ellison et al., "Diuretic Treatment in Heart Failure," New England Journal of Medicine, 377:1964-1975, 2017.
Hasselblad et al., "Relation Between Dose of Loop Diuretics and Outcomes in a Heart Failure Population: Results of the ESCAPE Trial", European Journal of Heart Failure, 9(10):1064-1069, 2007.
Marenzi et al., "Prevention of Contrast Nephropathy by Furosemide With Matched Hydration," JACC: Cardiovascular Interventions, 5(1):90-97, 2011.
Mendeley et al., "Furosemide", Science Direct, 5 p. 2016.
Oh et al., "Loop Diuretics in Clinical Practice," Review: Electrolyte Blood Press, 13(1): 5 pages, 2015.
Palazzuli et al. "Continuous versus bolus intermittent loop diuretic infusion in acutely decompensated heart failure: a prospective randomized trial," Critical Care 18, 2014.
Prandota et al., "Pharmacokinetics and metabolism of furosemide in man," European Journal of Drug Metabolism and Pharmcokinetics, 1(4): 5 pages, 1976.
Rosenberg et al., "Combination Therapy with Metolazone and Loop Diuretics in Outpatients with Refactory Heart Failure: An Observational Study and Review of the Literature," Cardiovascular Drugs and Therapy, Kluwer Academic Publishers, vol. 19, No. 4, Aug. 2005, 6 pages.
Testani et al., "Rapid and Highly Accurate Prediction of Poor Loop Diuretic Natriuretic Response in Patients with Heart Failure," Circulation; Heart Failure, vol. 9. No. 1, 2016, 32 pages.
Unknown Author, "Furosemide Drug Summary," Prescriber's Digital Reference, pp. 1-31, 2016.
Yeh et al., "Goal-directed diuresis: A case—control study of continuous furosemide infusion in critically ill trauma patients", The Journal of Emergencies, Trauma, and Shock, 8(1): 34-38, 2015.
Written Opinion of the International Searching Authority for PCT Application No. PCT/US2005/008948 dated Oct. 3, 2006, 3 pages.
Written Opinion of the International Searching Authority for PCT Application No. PCT/US2007/021791 dated May 8, 2008, 7 pages.
Written Opinion of the International Searching Authority for PCT Application No. PCT/U20S07/009685 dated Jul. 18, 2008, 10 pages.
Written Opinion of the International Searching Authority for PCT Application No. PCT/US2007/009684 dated Jul. 21, 2008, 7 pages.
Written Opinion of the International Searching Authority for PCT Application No. PCT/US2008/007845 dated Sep. 17, 2008, 5 pages.
Written Opinion of the International Searching Authority for PCT Application No. PCT/US2008/007841 dated Sep. 18, 2008 4 pages.
Written Opinion of the International Searching Authority for PCT Application No. PCT/US2007/009683 dated Nov. 24, 2008, 6 pages.
Written Opinion of the International Searching Authority for PCT Application No. PCT/US2009/002739 dated Jun. 19, 2009, 4 pages.
Written Opinion of the International Searching Authority for PCT Application No. PCT/US2010/000137 dated Mar. 16, 2010, 8 pages.
Written Opinion of the International Searching Authority for PCT Application No. PCT/US2015/020196, dated Jun. 12, 2015, 5 pages.

Bart et al., "Ultrafiltration in Decompensated Heart Failure With Cardiorenal Syndrome", The New England Journal of Medicine, Dec. 13, 2012, 9 pages, Massachusetts Medical Society.
Brezis et al., Hypoxia of the Renal Medulla—Its Implications for Disease, New England Journal of Medicine, vol. 322, No. 10, Mar. 9, 1995, 9 pages.
Briguori et al., "Renal Insufficiency After Contrast Media Administration Trial II (Remedial II): RenalGuard System in High-Risk Patients for Contrast-Induced Acute Kidney Injury", Circulation, Journal of the American Heart Association, Mar. 13, 2011, 10 pages.
Dorval et al., "Feasibility Study of the RenalGuard™ Balanced Hydration System: A Novel Strategy for the Prevention of Contrast-Induced Nephropathy in High Risk Patients", International Journal of Cardiology, 2011, 5 pages, Elsevier Ireland Ltd.
Edelson et al., Pharmacokinetics of Iohexol, a New Nonionic Radiocontrast Agent, in Humans, Journal of Pharmaceutical Sciences, vol. 73, No. 7, Jul. 1984, 3 pages.
Felker et al., "Diuretic Strategies in Patients With Acute Decompensated Heart Failure", The New England Journal of Medicine, Mar. 3, 2011, vol. 364, No. 9, 9 pages.
Gloor, James M. and Vincente E. Torres, Reflux and Obstructive Nephropathy, Atlas of Diseases of the Kidney, on-line edition, vol. Two, Section I, Ch. 8, pp. 8.1-8.25, 1999, 27 pages.
Hvistendahl et al., Renal Hemodynamic Response to Gradated Ureter Obstruction in the Pig, Nephron 1996, 74:168-74, 7 pages.
Lelarge et al., Acute Unilateral Renal Failure and Contralateral Ureteral Obstruction, American Journal of Kidney Diseases, vol. XX, No. 3, Sep. 1992, 3 pages.
Levin et al. High-volume diuresis with matched maintenance of intravascular volume may prevent contrast-induced nephropathy in post-transplant patients with moderate-severe baseline renal impairment, Cardiovascular Revascularization Medicine, Elsevier, NL, vol. 8, No. 2, Apr. 1, 2007, 1 page.
Lloyd-Jones et al., "Heart Disease and Stroke Statistics—2009 Update. A Report From the American Heart Association Statistics Committee and Stroke Statistics Subcommittee", Circulation, Journal of the American Heart Association, Jan. 27, 2009, 161 pages.
Marenzi et al.. "Prevention of Contrast Nephropathy by Furosemide With matched Hydration. The MYTHOS (Induced Diuresis With Matched Hydration Compared to Standard Hydration for Contrast Induced Nephropathy Prevention) Trial", JACC: Cardiovascular Interventions, vol. 5, No. 1, 2012 The American College of Cardiology Foundation, 8 pages.
Mawer et al., "Value of Forced Diuresis in Acute Barbiturate Poisoning", Jun. 29, 1968, British Medical Journal, 2, 4 pages.
Paterna et al., "Changes in Brain Natriuretic Peptide Levels and Bioelectrical Impedance Measurements After Treatment With High-Dose Furosemide and Hypertonic Saline Solution Versus High-Dose Furosemide Alone in Refractory Congestive Heart Failure", Journal of the American College of Cardiology, 2005, vol. 45, No. 12, 7 pages.
Pederson et al., Renal Water and Sodium Handling During Gradated Unilateral Ureter Obstruction, Scand J. Urol Nephrol, 2002, 36:163-72, 11 pages.
Rihal et al., Incidence and Prognostic Importance of Acute Renal Failure After Percutaneous Coronary Intervention, Circulation, May 14, 2002, 6 pages.
Rosamilia et al., Electromotive Drug Administration of Lidocaine and Dexamethasone Followed by Cystodistension in Women with Interstitial Cystitis, International Urogyecologyl Journal, Pelvic Floor Dysfunction 1997; 8: 142-5, 4 pages.
S215 Ultra Low Profile Single Point Load Cell—Strain Guage Sensors and Load Cells, Ultra-Low Profile Single Point Load Cell—S215, http://smdsensors.com/detail_pgs/s215.htm 2005, 3 pages.
Solomon et al., Effects of Saline, Mannitol, and Furosemide on Acute Decreases in Renal Function Induced by Radiocontrast Agents, The New England Journal of Medicine, vol. 331: 1416-1420, Nov. 24, 1994, No. 21, 5 pages.
Stevens, Melissa A., Md et al., A Prospective Randomized Trial of Prevention Measures in Patients at High Risk for Contrast Nephropathy, Results of the P.R.I.N.C.E. Study, Journal of American College of Cardiology, vol. 33, No. 2, Feb. 1999, 9 pages.

(56) References Cited

OTHER PUBLICATIONS

Stevenson et al., "Editorial Comment, Torrent or Torment From the Tubules?", Challenge of the Cardiorenal Connections, Journal of the American College of Cardiology, vol. 45, No. 12, 2005, 4 pages.
Wakelkamp et al., The influence of drug input rate on the development of tolerance to frusemide, Br. J. Clin. Pharmacol 1998, 46:479-487, 9 pages.
Weinstein et al., Potential deleterious Effect of Furosmide in Radiocontrast Nephropathy, Department of Medicine, Hadassah Univeristy Hospital, Mount Scopus, Jerusalem, Israel, Nephron 1992, 62: 413-415, pages.
Doty et al., Effect of Increased Renal Venous Pressure on Renal Function, The Journal of Trauma: Injury, Infection and Critical Care, vol. 47, No. 6, Dec. 1999, 4 pages.
Heyman et al., Pathophysiology of Radiocontrast Nephropathy: A Role for Medullary Hypoxia, Investigative Radiology, vol. 34, No. 11, Nov. 1999, 7 pages.

\* cited by examiner

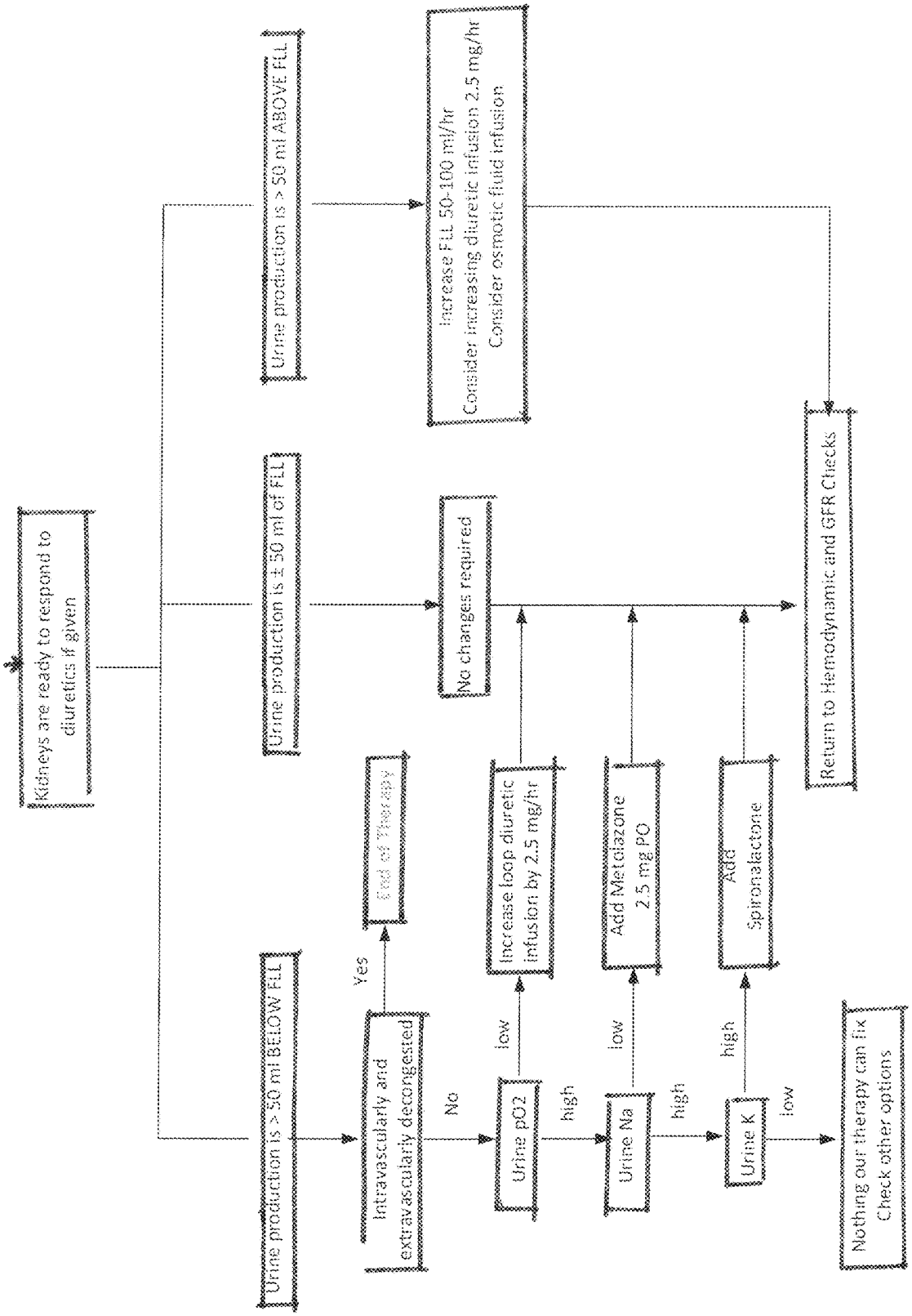

METHOD AND SYSTEM TO MONITOR URINE OUTPUT AND MANAGE FLUID RETENTION IN A PATIENT

RELATED APPLICATION

This application claims priority to U.S. provisional application 62/720,009, Filed Aug. 20, 2019, the entirety of which is incorporated by reference.

FIELD OF THE INVENTION

The field of the invention is monitoring urine output and managing a patient's fluid levels using a diuretic.

BACKGROUND OF THE INVENTION

The body of a healthy person naturally maintains a healthy balance of fluids. Patients often do not naturally achieve fluid balance when suffering from acute decompensated heart failure (ADHF), acute kidney injury (AKI) and other similar conditions. The kidneys in these patients are unable to generate sufficient urine to avoid fluid overload and maintain a proper fluid balance. A fluid overloaded patient is treated to reduce the fluid volume in the body, such as by receiving diuretics which promote urine output. Generally, fluid volume should be reduced in a rapid, safe and effective manner to reduce fluid levels (decongestion) in the patient.

Liquids normally represent about half to three-quarters of the body weight of a health person. Approximately two-thirds of the total liquid in a body are in the cells of the body (intracellular). The remaining one-third of total liquids are outside of the cells (extracellular). Most of the extracellular liquid bathes the cells (interstitial liquid). Another portion of extracellular liquid is in blood and circulates through the vascular system. The portion of total body liquid in the blood is typically about 7% of total body liquids. Wikipedia, Extracellular Fluid (Aug. 17, 2018). The body removes excess liquid primarily by generating urine. Secondary modes for removing liquids are by evaporation through skin such as sweating, discharge in feces, and evaporation from the lungs.

Artificially promoting urine production by administration of a diuretic is a well-known and standard practice for reducing fluid levels in a patient. The choice of type, amount and timing of diuretics affect the amount of urine that is produced and thus the rate at which fluid is removed from the body. Diuretics may be introduced by an intravenous (IV) line. If treatments with diuretics are unsuccessful, ultra-filtration may be used to reduce fluid levels to, for example, treat ADFH.

The short-term effects of diuretic administration on urine production for an individual are not entirely predictable. In response to a dose of a diuretic, a patient may produce much less urine than expected which may prolong a hospital stay or cause an outpatient to be hospitalized. Another patient may response to a dose of diuretic by producing excessive amounts of urine which raises concerns hypotension and vital organ damage.

The potential for substantially different responses and treatment outcomes in response to a dosage of diuretics creates uncertainties for physicians who have to determine correct diuretic dosing for an individual patient based on the patient's clinical signs and symptoms. Physicians may prescribe a conservative (low) diuretic dosage and later slowly increase the dose to achieve a desired urine output. This conservative approach can prolong the treatment and may render the patient unable to produce sufficient amounts of urine. Disadvantages of the conservative approach are that the patient's symptoms may be prolonged and the underlying clinical state may worsen due to the slow application of diuretics.

There is a long felt need to provide physicians with diagnostic information and recommended treatments for patients in a fluid overload condition and being treated to reduce the fluid volume in their body.

SUMMARY OF THE INVENTION

The inventors conceived of and disclose herein a novel method of treatment to reduce fluid levels in a fluid overloaded patient, such as one suffering from ADHF, AKI or other condition that results in fluid overload. The method including a regimen that: (i) determines whether the patient is suited for diuretic therapy, (ii) rapidly reduces the intravascular volume of fluid in the patient to a range below a threshold low level of intravascular volume and a hemodynamic level below which there is a risk of vital organ damage due to low intravascular volume, and (iii) maintains the intravascular volume in the range to allow extravascular fluid in the body to move into the vasculature and be removed by the kidneys generating urine.

The inventors invented a method to treat patients suffering from fluid overload including: administrating a diuretic to the patient to increase urine output of the patient; monitoring intravascular volume of the patient; and maintaining the patient in a condition in which the intravascular volume is below a baseline intravascular volume and above a hemodynamic level by adjusting the administered diuretic.

A physician prescribes diuretics that are administered to the patient to promote urine output. The physician selects the diuretic, dosage and timing of the administration of the dosage to achieve urine output that rapidly reduces intravascular volume and subsequently maintains intravascular volume in the range.

A fluid management device, such as the RenalGuard® system may be used to monitor urine output and promote urine output by injecting a hydration fluid into the patient and monitoring urine output. The injection of the fluid is controlled by monitoring urine output and using urine output as feedback to control the amount of fluid added to the patient. The fluid management device controls the amount of fluid added to the patient such that there is a net reduction in the amount of fluid in the patient. The fluid management device may also detect if the patient is not producing sufficient amounts of urine in response to diuretics and then automatically stops fluid injection and issues an alert suggesting that other treatments, such as ultrafiltration, may be appropriate.

The information provided by the urine monitoring device may be used to determine if a fluid overloaded patient should be treated with diuretics to promote urine output, whether administered diuretics are causing the kidneys to generate urine, whether a dosage of diuretics should be adjusted, whether a fluid should be infused into the patient to promote kidney functioning or otherwise assist the patient, and whether the patient is becoming hypotensive or otherwise suffer problems associated with unnaturally low intravascular fluid levels.

The invention may also be embodied as a method to reduce liquid levels of a patient comprising: determining a maximum liquid loss limit for the patient; monitoring urine output by the patient; infusing a hydration liquid into the patient; determining a net rate of liquid removal from the patient based on a difference between the urine output and the infusion of the hydration liquid, and automatically adjusting the infusion of the hydration liquid to maintain the net rate of liquid removal below the maximum liquid loss limit.

The maximum liquid loss limit may be a maximum net rate of liquid lost by the patient. The infusion of the hydration liquid and the automatic adjusting of the infusion of the hydration liquid may be performed using a hydration liquid system including an infusion controller configured to control a pump configured to pump the hydration liquid into the patient.

The infusion of the hydration liquid into the patient may initially be at a high rate which is greater than the urine output, and the high rate is late reduced to below the urine output. The high rate of hydration fluid may be reduced in response to the urine output exceeding a predetermined high threshold rate.

The infusion of the hydration liquid at the high rate may be performed by automatically infusing the hydration liquid at a high rate greater than a concurrent rate of urine output while the concurrent rate of urine output is below a threshold urine rate, and automatically reducing the high rate of the hydration liquid to below the concurrent rate of urine output in response to the concurrent rate of the urine output exceeding the threshold urine rate.

The invention may also be embodied as a method to reduce liquid levels of a patient comprising: repeatedly determining a current urine rate by the patient; initially infusing a hydration liquid into the patient at a high hydration rate greater than the current urine rate; and reducing rate of infusion of the hydration liquid to a rate below the current urine rate in response to the current urine rate exceeding a predetermined high threshold rate.

The determination of the current urine rate may be performed at intervals of no greater than five minutes.

The method may include administering a diuretic to the patient while infusing the hydration liquid at the high hydration rate.

The method may further include: determining a net rate of liquid removal from the patient based on a difference between the urine output rate and a rate of the infusion of the hydration liquid, and automatically adjusting the infusion of the hydration liquid to maintain the net rate of liquid removal below a maximum liquid loss limit.

BRIEF DESCRIPTION OF THE DRAWINGS

The following figures illustrate the invention and is use:

FIGS. 3 and 4 are a flow chart of an exemplary optimization phase of the regimen.

DETAILED DESCRIPTION OF THE INVENTION

Figure 1:
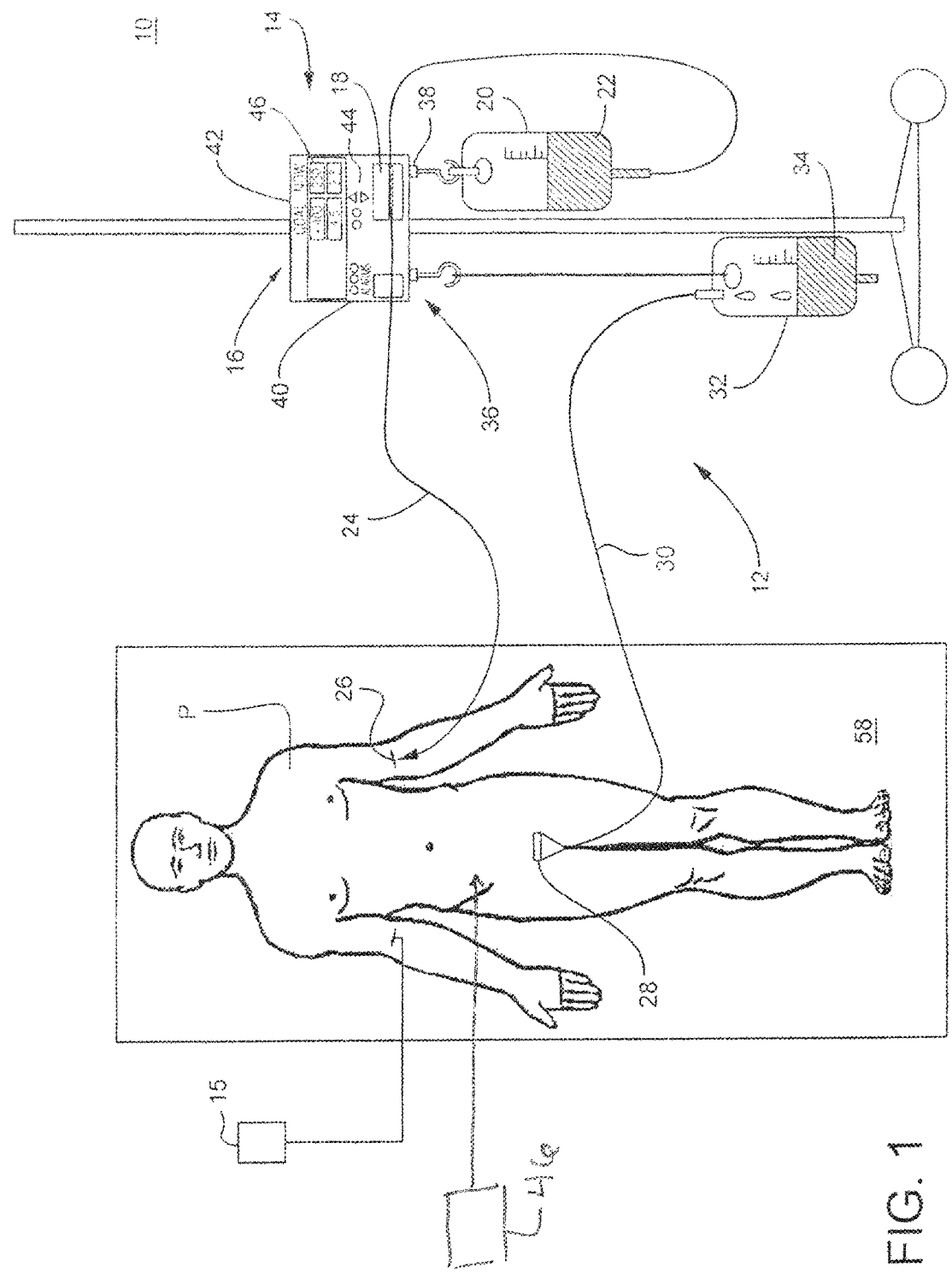
FIG. 1 is a schematic view of one embodiment of a patient hydration system which is configured to monitor urine output and control the injection of a fluid into a patient.

FIG. 1 shows a patient fluid management system 10 that includes a urine collection system 12 and an optional hydration fluid infusion system 14 both of which are connected to patient P. The patient is suffering from fluid overload and may be hospitalized and receiving diuretics 15 through an intravenous (IV) line. The diuretics may be added to a line injecting the hydration fluid or may be added to another saline solution filled bag 15 connected to the patient via another IV line.

The optional hydration fluid infusion system 14 includes an infusion controller 16, that includes an infusion pump 18, e.g., a peristaltic pump, connected to a fluid source 20, e.g., saline bag, of an hydration fluid 22, e.g. saline, by tubing (line) 24. An intravenous (I.V.) needle 26 is inserted in a vein of the patient P and is connected to infusion pump 18 via tubing 24. Fluid 22 from the source 20 flows through the tubing 24 and I.V. needle 26 directly into a blood vessel, e.g., peripheral vein, of the patient P. The amount or rate of fluid(s) 22 flowing into the patient may be determined by the pumping rate or number of rotations the infusion pump 18.

The urine collection system 12 includes a catheter 28, such as a Foley catheter, placed in the bladder of patient P. Tubing 30 connects catheter 28 to a urine collection device, such as a bag 32. The urine 34 collected in the bag 32 is weighed or otherwise measured by a weight scale 36 or other urine flow measurement device which communicates with the infusion controller 16. A weight scale 38 may also weight the hydration fluid 22.

The amount or rate of urine 34 is monitored in real time by the infusion controller 16. Similarly, the amount of hydration fluid 22 in the fluid source 20 may be monitored or measured by a weight scale 38. The weight scales 36, 38 may be a single weight scale which measures the combined change in urine output and fluid input by and to the patient. The combined change in urine output and fluid input indicates the net fluid loss or gain by the patient.

The infusion controller 16 monitors the weight of the hydration fluid 22, the amount of the hydration fluid 22 pumped through pump 18 or otherwise monitors, in real time, the amount or rate of hydration fluid 22 flowing into the patient P.

The fluid management system 10 may be the RenalGuard System®, developed and marketed by RenalGuard Solutions, Inc. of Milford, Massachusetts, which in the past has been used to protect patients from kidney injury during procedures that require iodinated contrast agents.

A computer control system 40 in the infusion controller 16 receives an input as to a desired negative fluid balance, and/or amount(s) or rate(s) of urine output and/or of a desired amount(s) or rate(s) of a difference urine output and the amount of hydration fluid. A negative fluid balance refers to injecting less hydration fluid 22, in terms of mass or flow rate, into the patient than the amount of urine 34 output. The fluid balance may be repeatedly determined, such as every thirty minutes, every hour or every few hours. During the treatment period, the amount of hydration fluid injected into the patient may initially be greater than the amount of urine output, in an effort to start a high urine output flow. Later in the treatment period, such as after the urine output flow reaches a predetermined high threshold rate, the rate of infusion of the hydration fluid may be reduced. The high urine output flow is expected to continue after the reduction of the rate of the hydration fluid.

The computer control system 40 may include a processor (s) and a non-transient memory configured to store program instructions, settings for the patient fluid management system 10 and data collected from or calculated by the computer control system 40. The data may include urine output volume or rate of urine output, amount of fluid infused into the patient and rate of infusion, the amount and rate of injection of a diuretic, the weight of the patient at various times during the infusion of the fluid, and the time during which the patient is treated with the patient fluid management system 10. The computer control system 40 may include a console 42 having a user input device 44, such as a key pad, and a user output device 46, such as a computer display.

The input device 44 may be used to input certain parameters of the treatment sessions, such as a desired fluid balance level, desired urine output level, and the planned duration of the input balance level or urine output level. Another input may be the amount of fluids during the treatment session received by the patient through means other than the fluid source 20. For example, the input device 44 may be configured to receive inputs indicating the amount of fluid included with a saline filled bag 15 used to inject the diuretic into the patient.

Figure 2:
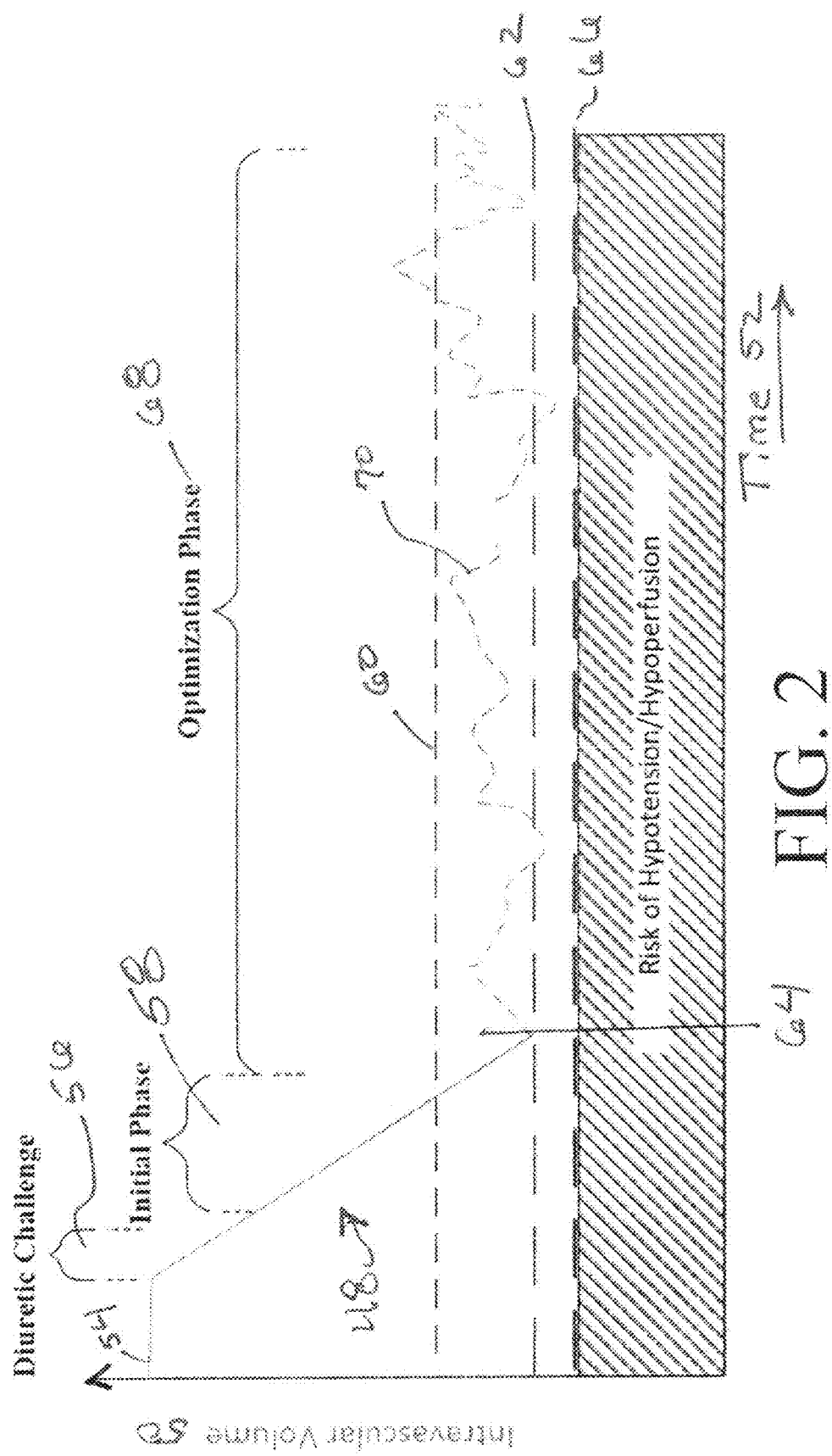
FIG. 2 is a graphical representation of a regimen for treating fluid overload.

FIG. 2 is a diagram illustrating an exemplarily regimen to reduce fluid levels in a patient suffering from fluid overload. The diagram shows the relationship between a desired target 48 intravascular volume (horizontal axis 50) and time (vertical axis 52). The intravascular volume is the fluid (blood plasma) in the vasculature of the body.

Intravascular volume is used in FIG. 2 to illustrate a desired therapeutic effect of administering a diuretic and promoting urine output. Intravascular volume is measured using a system 46 that measures a parameter of the patient from which intravascular volume can be calculated or estimated. Moreover, other parameters from which intravascular volume or a change in such volume may be calculated or estimated include: measuring urine output, calculating net fluid loss (urine output minus fluid intake); measuring central venous pressure (CVP), measuring renal perfusion pressure, and measurements of concentrations of chemicals in urine such as the partial pressure of oxygen in urine, potassium, sodium and keratein.

A patient in a fluid overloaded condition as indicated by an excessive intravascular fluid level 54 is a candidate for the regimen shown in FIG. 2. During an initial phase 56 of the regimen, an evaluation is made as to whether the patient sufficiently responds to a diuretic. An initial dose of a diuretic may be administered, and the urine output is monitored to determine if there is sufficient increase in urine output rate in response to the diuretic. For example, a goal of having the patient excrete at least 200 ml of urine within four (4) hours of receiving a dose of a diuretic may be used to determine if the patient is suited for proceeding beyond the diuretic challenge 56 and to the initial phase 58.

If the patient is responsive to a diuretic to promote urine output, a dose of a diuretic is applied to cause a high urine output during an initial phase 58 of the regimen. During the initial phase, urine output is increased to cause the intravascular volume 48 to fall below the normal base line 60 for intravascular volume and to a target minimum level 62 for intravascular volume.

The current level of intravascular volume is determined based measurements of blood pressure, cardiac output and/or systemic vascular resistance. The measurements may be performed by a system 46 configured to measure one or more of blood pressure, cardiac output and systemic vascular resistance. These measurements may be performed continuously or at regular intervals, such as every 10 minutes, 30 minutes or hourly. An example of a monitoring system to sense parameters indicative of intravascular volume and/or changes in intravascular volume is an intrathoracic impedance monitoring (such as may be included in an implanted defibrillator or biventricular pacing device).

During the initial phase, the rate of net fluid volume removal may be controlled by the fluid management system to be at a fluid loss limit (FLL) rate or at a rate offset by a selected safeguard for the FLL. The FLL is a maximum rate of net volume removal the fluid management system will target. The FLL may be defined clinically as a rate which the physician determines as rate of net amount of fluid volume removal from the patient without adverse hemodynamic changes or activation of central SNS or renal salt and water retaining mechanisms.

The fluid management system may automatically infuse the hydration fluid to ensure that the FLL is not exceeded. For example, if the kidneys are producing urine at a rate of 500 ml/hour and the FLL is set to a rate of 200 ml/hour, the system will infuse replacement fluid at a rate of 300 ml/hour. If urine production is below the FLL rate, the fluid management system may not infuse a hydration fluid or may infuse the hydration fluid at a rate intended to ensure that renal perfusion pressure is sufficient to promote generation of urine by the kidneys.

The base line is the amount of intravascular volume (blood plasma) that the patient would have when healthy and properly functioning kidneys.

The target minimum intravascular level 62 is defined clinically as the minimum level of intravascular volume that can maintain sufficient cardiac output to allow adequate renal perfusion. Alternatively, the target minimum intravascular level 62 may be defined physiologically as a 10% decrease in cardiac output as compared to the cardiac output at the base line 60 and/or a 10% increase in systemic vascular resistance from that at the baseline (60).

The rapid reduction in intravascular volume is intended to stop at time 62 which is when the intravascular volume reaches the target minimum intravascular level. The reduction in intravascular volume may be achieved by reduction in the type or dosage of the diuretic and/or by increasing the infusion rate of a hydration fluid 22. The infusion controller 16 may monitor in real time or by receiving user inputs an indicator(s) of intravascular volume and automatically increase (or start) the infusion rate of the hydration fluid. Similarly, the physician may manually increase the rate of the infusion fluid and adjust the type and/or dosage of the diuretic to slow or halt the reduction in intravascular fluid.

Figure 3:
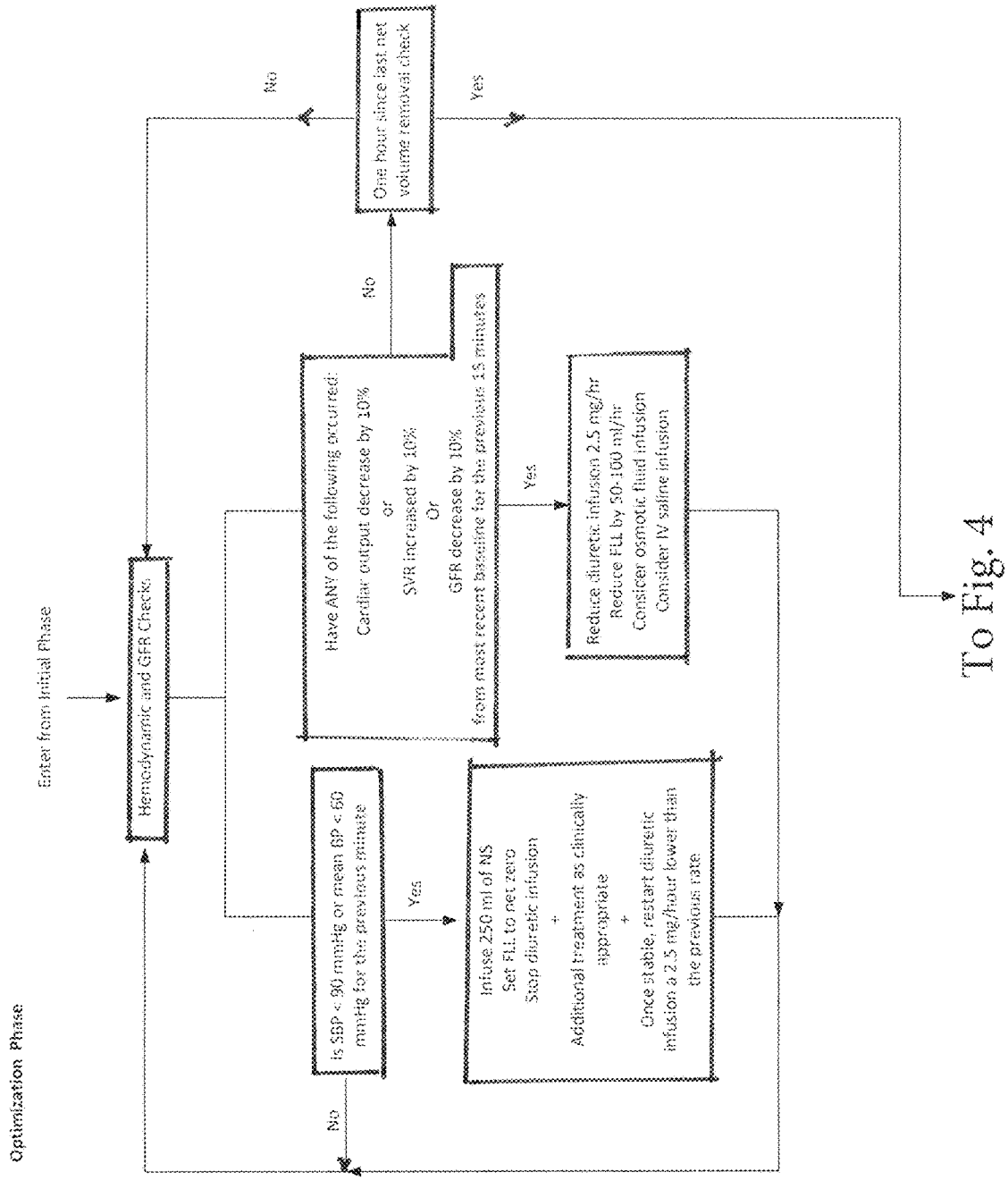

As shown in FIGS. 3 and 4, the optimization phase 68 of the regimen maintains the current intravascular volume 70 (FIG. 2) between the baseline intravascular volume 60 and the hemodynamic level 66. The optimization phase operates to keep the current intravascular volume 70 at the target minimum intravascular volume 62.

During the initial phase, it is believed that the liquid in the vascular system is reduced as the kidneys produce urine. Other liquids in the body (interstitial and intracellular liquids) are slow to move into the vasculature. During at least an early portion of the initial phase, the interstitial and intracellular liquids are not flowing rapidly into the vasculature and thus the amount of liquid in the vascular volume drops rapidly as the urine rate is increased due to the diuretic. Moreover, the flow of interstitial and intracellular fluids into the vascular volume may remain at or below a maximum urine rate that can be achieved with aggressive dosages of a diuretic. Thus, during the optimization phase 68, the dosage of the diuretic and the infusion of the hydration fluid may be controlled to cause a urine rate that is commiserate, e.g., approximately equal too, the predicted rate at which interstitial and intracellular fluids enter the vascular volume.

During an optimization phase 68, the current intravascular volume level 70 moves above and below the target level 62. During this phase, the patient remains under treatment by a diuretic. Also, the fluid management system adjusts the infusion of the hydration fluid to achieve desired levels of urine output and negative fluid balance in the patient. During the optimization phase 68, the PRR is expected to be the high end at or slightly above a predefined range, such as 100 to 300 ml/hour.

During the optimization phase, the physician prescribes a diuretic and dosage which is intended to maintain the current intravascular volume level 70 at the target minimum intravascular volume 62. If the current intravascular volume level 70 is consistently below the target 62, the patient may be in an over-diuresis condition due to excessive urine output as compared to the rate at which interstitial and intracellular fluids move into the vascular volume to replace liquid (blood plasma) removed from the vascular volume due to urine. A patient that is in an over-diuresis condition may be a candidate to have a lower dosage of the diuretic or another less aggressive diuretic.

If the current intravascular volume level 70 is consistently above the target, the patient may be in an under-diuresis condition in which the urine output is insufficient to maintain the target 62 vascular volume. A patient that is in an under diuresis condition may be a candidate to receive a higher dosage of diuretic or a more aggressive diuretic.

Adjusting the diuretic type/dosage and/or the infusion of a hydration fluid is used to keep the intravascular volume 48 above a level 66 of an at-risk intravascular volume level. The at-risk intravascular volume level is a minimum volume below which the patient is at risk for vital organ damage, and/or the systolic arterial blood pressure is less than 90 mmHg and/or a mean arterial blood pressure is less than 60 mmHg. The intention is to maintain the intravascular fluid level always above the level 66 at which there is a risk of hypotension and/or hypoperfusion. In a fluid overload patient, there are excessive body liquids (interstitial and intracellular) beyond the liquids in the intravascular volume. These excess liquids should be removed to treat the fluid overload condition.

The regimen proposed in FIG. 2 removes these other excessive body liquids (interstitial and intracellular) by holding the intravascular volume at levels below baseline 60 and at or near a target level 62. Because the intravascular volume is well below the baseline 60, the remaining body liquids will tend to more rapidly flow into the vasculature as the body attempts to increase the vascular volume to at least the base line. The flow of the remaining body fluids into the vascular volume is the plasma refilling rate (PRR).

The fluid management system 14 monitors the net removal of fluids from the body, such as by measuring the urine output and the hydration liquid input (and possibly inputs from other liquids). The fluid management system may produce alerts or reports that the patient is in an under-diuresis or over-diuresis condition. The physician, with the assistance of the fluid management system, may modify the diuretic or its dosage to treat the under-diuresis or will continue the regimen until a desired fluid balance is achieved in the patient.

The fluid management system 14 may also automatically adjust the pumping rate of the hydration fluid or generate a report of suggested pumping rates. The fluid management system 14 may automatically increase the pumping rate of the hydration fluid in response to a determination that the current intravascular volume 70 is below the target minimum 62. The amount of increase in the rate of the hydration fluid may be proportional to the difference between the current intravascular volume 70 and the target minimum 62 or proportional to a difference between the current intravascular volume 70 and the at-risk intravascular volume level 66.

The optimization phase 68 continues until the patient has been decongested such that the total body fluid is within a desired range.

Although specific features of the invention are shown in some drawings and not in others, this is for convenience only as each feature may be combined with any or all of the other features in accordance with the invention. For example, there are other ways to determine a patient's urine output and other ways to quantify the amount of hydration fluid administered to the patient. There are also other ways to redundantly check the amount of hydration fluid administered the patient. Also, the words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

The invention claimed is:

1. A method to reduce liquid levels of a patient, the method comprising:
   monitoring urine output by the patient;
   infusing a hydration liquid configured to prevent or treat dehydration into the patient;
   determining a net rate of liquid removal from the patient based on a difference between the urine output and the infusion of the hydration liquid,
   obtaining a first intravascular volume level of the patient that corresponds to a baseline intravascular volume level;
   obtaining a second intravascular volume level of the patient that corresponds to an at risk intravascular volume level;
   during a first period, causing the infusion of the hydration liquid at a first hydration rate greater than a rate of the urine output to reduce an intravascular fluid volume of the patient, and
   during a second period after the rate of the urine output reaches or exceeds a predetermined urine output threshold, adjusting the infusion of the hydration liquid to be a second hydration rate different than the first hydration rate and less than the rate of the urine output, wherein, during the second period, the intravascular fluid volume of the patient remains between the first intravascular volume level and the second intravascular volume level.

2. The method of claim 1, wherein causing the infusion of the hydration liquid at the first hydration rate comprises maintaining the net rate of liquid removal below a maximum liquid loss limit or a maximum rate of liquid lost.

3. The method of claim 1, wherein causing the infusion of the hydration liquid and adjusting the infusion of the hydration liquid are performed by an infusion controller configured to control a pump configured to be fluidly coupled to the hydration liquid.

4. The method of claim 1, wherein the first hydration rate is greater than the second hydration rate.

5. The method of claim 1, wherein the at risk intravascular volume level corresponds to a hemodynamic fluid level of the patient below which there is a risk of vital organ damage to the patient.

6. The method of claim 1, further comprising administering a diuretic to the patient concurrently with at least a portion of the first period or the second period.

7. The method of claim 1 wherein the infusion of the hydration liquid at the second hydration rate, together with a dosage of a diuretic, causes the rate of urine output to be equal to a predicted rate at which interstitial and intracellular fluids enter the patient's intravascular volume.

\* \* \* \* \*